(12) United States Patent
Vane et al.

(10) Patent No.: US 8,114,255 B2
(45) Date of Patent: Feb. 14, 2012

(54) MEMBRANE-AUGMENTED DISTILLATION WITH COMPRESSION TO SEPARATE SOLVENTS FROM WATER

(75) Inventors: Leland M Vane, Cincinnati, OH (US);
Franklin R Alvarez, Cincinnati, OH (US); Yu Huang, Palo Alto, CA (US);
Richard W Baker, Palo Alto, CA (US)

(73) Assignee: Membrane Technology & Research, Inc., Menlo Park, CA (US)

( * ) Notice: Subject to any disclaimer, the term of this patent is extended or adjusted under 35 U.S.C. 154(b) by 194 days.

(21) Appl. No.: 12/229,802

(22) Filed: Aug. 27, 2008

(65) Prior Publication Data

US 2010/0051441 A1 Mar. 4, 2010

(51) Int. Cl.
*B01D 3/00* (2006.01)
*C07C 45/82* (2006.01)
*C07C 29/80* (2006.01)
*C07C 51/44* (2006.01)

(52) U.S. Cl. .............. 203/12; 203/15; 203/16; 203/17; 203/18; 203/19; 203/23; 203/24; 203/25; 203/26; 203/27; 203/75; 203/78; 203/DIG. 8; 203/DIG. 9; 203/DIG. 13; 210/640; 210/641; 435/162; 435/163; 568/916

(58) Field of Classification Search ............... 203/3, 12, 203/15–19, 23–27, 39, 75, 78, DIG. 8, DIG. 9, 203/DIG. 13; 210/640, 641; 435/162, 163; 568/916
See application file for complete search history.

(56) References Cited

U.S. PATENT DOCUMENTS

| | | | | |
|---|---|---|---|---|
| 4,217,178 A * | 8/1980 | Katzen et al. | | 203/19 |
| 4,294,664 A * | 10/1981 | Anthony | | 203/19 |
| 4,340,446 A * | 7/1982 | Crawford | | 203/19 |
| 4,372,822 A * | 2/1983 | Muller et al. | | 203/19 |
| 4,405,409 A | 9/1983 | Tusel et al. | | |
| 4,422,903 A * | 12/1983 | Messick et al. | | 203/19 |
| 4,539,076 A | 9/1985 | Swain | | |
| 4,978,430 A | 12/1990 | Nakagawa | | |
| 5,035,776 A | 7/1991 | Knapp | | |
| 5,105,029 A | 4/1992 | Ninomiya et al. | | |
| 5,124,004 A * | 6/1992 | Grethlein et al. | | 203/19 |
| 6,551,466 B1 * | 4/2003 | Kresnyak et al. | | 203/1 |
| 7,297,236 B1 | 11/2007 | Vander Griend | | |
| 7,744,727 B2 * | 6/2010 | Blum et al. | | 203/19 |
| 2006/0070867 A1 | 4/2006 | Wu et al. | | |
| 2007/0000769 A1 * | 1/2007 | Brown | | 203/19 |
| 2009/0057128 A1 * | 3/2009 | Vane et al. | | 203/17 |
| 2009/0215139 A1 * | 8/2009 | Datta et al. | | 435/162 |

* cited by examiner

*Primary Examiner* — Virginia Manoharan
(74) *Attorney, Agent, or Firm* — J. Farrant; K. Bean

(57) ABSTRACT

Processes for removing water from organic solvents, such as ethanol. The processes include distillation in two columns operated at sequentially higher pressure, followed by treatment of the overhead vapor by one or two membrane separation steps.

43 Claims, 8 Drawing Sheets

MEMBRANE-AUGMENTED DISTILLATION WITH COMPRESSION TO SEPARATE SOLVENTS FROM WATER

This invention was made in part with Government support under a Cooperative Research and Development Agreement (CRADA) between the United States Environmental Protection Agency and Membrane Technology and Research, Inc. The Government has certain rights in this invention.

FIELD OF THE INVENTION

The invention relates to production and dehydration of solvents, especially alcohols. In particular, the invention relates to combinations of distillation, overhead vapor compression and membrane separation to produce a dehydrated solvent product.

BACKGROUND OF THE INVENTION

The production of dry solvents from raw aqueous mixtures is often costly and complicated. The preparation of dry ethanol is a good example. In the conventional process, the raw fermentation broth is stripped under moderate vacuum in a beer still. Overhead vapor from the beer still is sent to a rectification column that produces an overhead product close to the azeotrope (about 93 wt % ethanol) and a bottoms product, which is essentially water. The condensed product from the top of the column is evaporated under pressure and fed to a molecular sieve dryer, which produces ethanol of 99 wt %+purity. Such a process consumes almost 100 million Btu/h/h to produce 50 million gallons per year of purified ethanol from a feed containing about 11 wt % ethanol.

It is known to use two distillation columns in series to separate mixtures such as organic/water mixtures. Such processes are taught in U.S. Pat. Nos. 4,539,076; 5,035,776; and 7,297,236, for example.

It is also known to use membrane separation to treat the overhead stream from a column. Such processes are taught in U.S. Pat. No. 4,978,430; in U.S. Published Application number 2006/0070867; in Japanese Published Application number JP7227517; and in U.S. patent application Ser. No. 11/896,201.

In addition, co-owned U.S. Pat. No. 7,732,173, issued Jun. 8, 2010, to Mairal et al., teaches a process for recovering ethanol involving membrane separation, followed by dephlegmation, followed by a second membrane separation step to dehydrate the overhead stream from the dephlegmator.

U.S. Pat. No. 5,105,029 teaches the use of two columns followed by membrane separation; and U.S. Pat. No. 4,405,409 discloses the use of two membrane separation steps in series to treat a column overhead.

Specific membranes for use in dehydration of organic compounds are taught in co-owned U.S. Pat. No. 8,002,874, issued Aug. 23, 2011, to Huang et al., and co-owned and copending U.S. application Ser. No. 11/897,675.

Despite the extensive efforts represented by the prior literature, there remains a need for a process that is both energy efficient and cost effective for producing high purity dehydrated solvents, especially ethanol.

SUMMARY OF THE INVENTION

The invention is a process for dehydrating solvents, particularly solvents that are readily miscible with water, and especially ethanol.

The process incorporates two distillation steps in series, operated at different pressures, followed by one or two membrane separation steps. The steps are integrated in such a way as to provide an operation that has both good energy efficiency and controlled capital costs.

In a basic embodiment, the process of the invention includes the following steps:
(a) subjecting at least a portion of solvent and water mixture to a first distillation step, carried out by passing a first feed stream of the mixture, at a first pressure, into a first column having a reboiler system, to produce a solvent-enriched, first overhead vapor stream and a bottoms stream;
(b) compressing at least a portion of the first overhead vapor stream to form a compressed overhead vapor stream;
(c) subjecting the compressed overhead vapor stream to a second distillation step, carried out at a second pressure that is higher than the first pressure, in a second column having a reflux condenser system, to produce a solvent-enriched, second overhead vapor stream;
(d) performing a first membrane separation step, comprising:
(i) providing a first membrane having a first feed side and a first permeate side, the membrane being selective in favor of water over solvent;
(ii) passing at least a portion of the second overhead vapor stream at a first feed pressure across the first feed side;
(iii) maintaining a first permeate pressure on the first permeate side that is lower than the first feed pressure;
(iv) withdrawing from the first feed side, as a first residue stream, a dehydrated solvent product;
(v) withdrawing from the first permeate side a first permeate stream enriched in water compared with the second overhead vapor stream;
(e) recovering heat by:
(i) providing a heat exchanger that forms at least part of the reflux condenser system and at least part of the reboiler system;
(ii) passing a reflux stream withdrawn from the second column through the heat exchanger;
(iii) passing a reboil stream withdrawn from the first column through the heat exchanger in heat exchanging relationship with the reflux stream; and
(f) recirculating the first permeate stream within the process to a distillation step selected from the group consisting of the first distillation step and the second distillation step.

The first distillation step may be carried out solely as a stripping step. Alternatively, the column may include a reflux condenser, so that rectification also takes place in the column. The first distillation step is carried out at lower pressure than the second step, and optionally may be carried out at subatmospheric pressure, such as 0.5 bar or less.

The overhead vapor from the first column is compressed and sent as vapor to the second distillation step. Use of a compressor not only provides a higher pressure operating environment for the second column, but provides driving force for the membrane separation step(s).

The second distillation step may be carried out using only rectification or dephlegmation. Alternatively, the column may include a reboiler, so that stripping also takes place in the column. The second distillation step is carried out at a higher pressure than the first step, and may be carried out at above atmospheric pressure, such as at 2 or 3 bar.

Because the second column operates at a higher pressure, it is possible, and preferable, although not essential, to recover energy within the process by using a heat exchanger that serves as at least part of the reflux condenser of the second column and the reboiler of the first column. In this manner, latent and sensible heat from the overhead of the second column is used to heat the reboil stream for the first column.

In many cases, the heat energy recovered by condensing the reflux of the second column more than compensates for the energy required to run the compressor between the columns.

Additional heat energy can be recovered by condensing the membrane residue product stream by heat exchange against the reboil stream. The remainder of the heat energy needed to operate the reboiler may be provided by steam, for example. If heat energy from the membrane residue stream is not used, or is only partially used, in the reboiler, heat energy may optionally be recovered from this stream by condensing the product stream in a heat exchanger against the raw incoming feed stream.

The overhead from the second column is sent as feed to the membrane separation step. Optionally, the overhead may be further compressed before it is sent to the membranes.

The membrane separation step operates under a pressure difference between the feed and permeate sides of the membranes. The step divides the overhead stream into a residue stream, which is the dehydrated product of the process, and a permeate stream. To increase the driving force for transmembrane permeation, it is preferred to maintain the permeate side of the membranes under a partial vacuum. This also improves the pressure ratio for this step, which makes for a better separation between stream components.

The pressure ratio may be increased by using a vacuum pump in the permeate line to pull a vacuum on the permeate side. Preferably, the permeate stream is condensed, thereby creating the desired partial vacuum. The condensed stream is then passed to the first or second distillation step in liquid form. Return of the permeate in either vapor or liquid form within the process increases the overall heat recovery.

The residue stream is withdrawn from the process, optionally after heat recovery as mentioned above.

Overall, the options for heat recovery that may be used within the process include, but are not limited to: heat exchange between the reflux of the second column and the reboil stream of the first column; heat exchange between the product stream and the first column reboil stream or the feed stream; heat exchange between the permeate streams and the first column reboil stream or the feed stream; and heat exchange between the bottoms stream from the second column and the first column reboil stream or the feed stream. Any one of these, and preferably several, or most preferably all of these, may be used within the scope of the invention.

More than one membrane separation step may optionally be used. Use of two membrane separation steps, with the residue from the first step forming the feed to the second, provides greater flexibility to tailor the process to control total energy usage and compressor capacity. This means there is also more flexibility in terms of the heat exchange choices when two membrane separation steps are used.

The raw solvent/water mixture to be treated may enter the process by passing into the first distillation step. It is also within the scope of the invention to split the raw feed, so that one portion is sent to the first column and another portion is sent to the second column. This type of embodiment can provide processes that combine low energy usage with modest compressor capacity in such operations as the production of bioethanol.

It is also possible to use the process of the invention to treat two different feed mixtures simultaneously. For example, a plant processing both ethanol made from corn and ethanol made from cellulosic material can use the process of the invention in an energy-saving manner by sending the raw corn-based stream directly to the first column and the raw cellulose-based stream directly to the second column.

Optionally, a variant of the process may be carried out with heat exchange between the columns taking place within the second column itself, rather than in an external reboiler. In other words, the reboil stream from the first column is directed as a cooling medium into the second column. In this case, the second column can take the form of a simple shell-and-tube dephlegmator, for example.

The processes of the invention can treat streams of any solvent/water composition, but are particularly suited to treating those in which the solvent is present at low concentrations, such as below 15 wt %, below 10 wt % or even below 5 wt %, such as only 1 wt % or 3 wt %. For the lowest solvent concentration feeds, designs with two membrane steps are especially beneficial.

In another aspect, the invention is a process for producing light alcohols, such as methanol, ethanol and butanol, by fermentation. The invention in this aspect includes the following steps:

(a) fermenting a sugar to form a fermentation broth comprising the alcohol and water;
(b) subjecting at least a portion of the fermentation broth to a first distillation step, carried out by passing a first feed stream of the fermentation broth, at a first pressure, into a first column having a reboiler system, to produce an alcohol-enriched, first overhead vapor stream and a bottoms stream;
(c) compressing at least a portion of the first overhead vapor stream to form a compressed overhead vapor stream;
(d) subjecting the compressed overhead vapor stream to a second distillation step, carried out at a second pressure that is higher than the first pressure, in a second column having a reflux condenser system, to produce an alcohol-enriched, second overhead vapor stream;
(e) performing a first membrane separation step, comprising:
(i) providing a first membrane having a first feed side and a first permeate side, the membrane being selective in favor of water over alcohol;
(ii) passing at least a portion of the second overhead vapor stream at a first feed pressure across the first feed side;
(iii) maintaining a first permeate pressure on the first permeate side that is lower than the first feed pressure;
(iv) withdrawing from the first feed side, as a first residue stream, a dehydrated alcohol product;
(v) withdrawing from the first permeate side a first permeate stream enriched in water compared with the second overhead vapor stream;
(f) recovering heat by:
(i) providing a heat exchanger that forms at least part of the reflux condenser system and at least part of the reboiler system;
(ii) passing a reflux stream withdrawn from the second column through the heat exchanger;
(iii) passing a reboil stream withdrawn from the first column through the heat exchanger in heat exchanging relationship with the reflux stream;
(g) recirculating the first permeate stream within the process to a destination selected from the group consisting of the fermentation step (a), the first distillation step (b) and the second distillation step (d).

The fermentation step involves fermenting a sugar with any organism suitable for fermenting that sugar. The sugar may be from any source, including those formed by conversion of starchy, cellulosic and lignocellulosic materials.

In this process, it is possible to return the permeate stream, or one of the permeate streams if two membrane separation steps are used, to the fermentation step.

It is to be understood that the above summary and the following detailed description are intended to explain and illustrate the invention without restricting its scope.

DETAILED DESCRIPTION OF THE INVENTION

Figure 1:
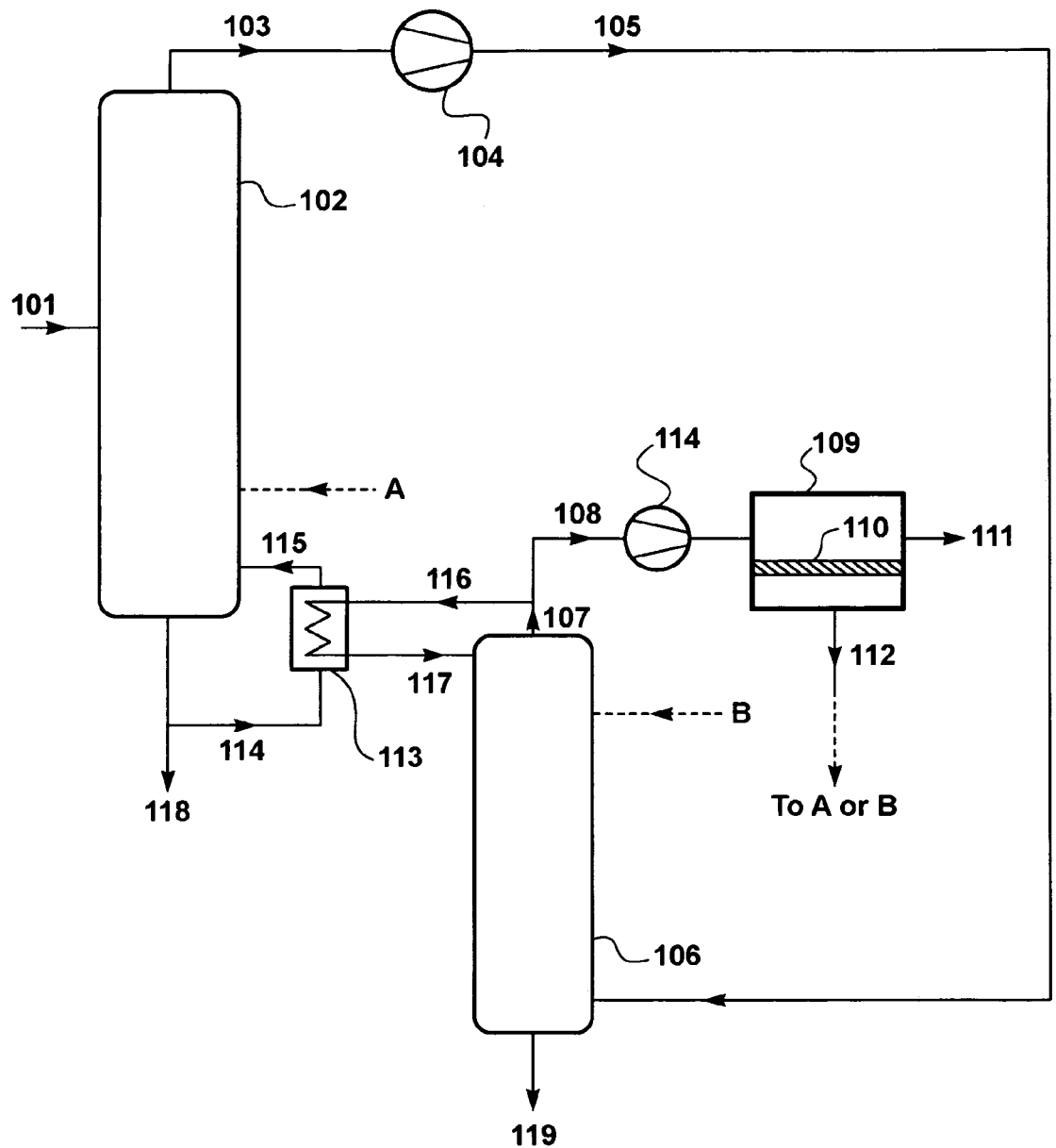
FIG. 1 is a schematic drawing showing the process flow scheme and apparatus elements for a basic embodiment of the invention.

The terms solvent/water solution and solvent/water mixture used herein refer to any mixtures or solutions of any organic compound and water that are generally liquid at room temperature and pressure, but that may be in the liquid or vapor phase during operation of the process.

The term selectivity as used herein refers to the selectivity of a membrane expressed as the ratio (water permeance)/(solvent permeance), as measured with membrane samples and with the solvent/water mixture of interest at the operating temperature at which the process is to be carried out.

The term rectification as used herein means composition adjustment of vapor by contact and interaction with condensed liquid.

The term stripping as used herein means composition adjustment of liquid by contact and interaction with evaporated vapor.

All liquid mixture percentages herein are by weight unless otherwise stated. Gas or vapor mixture percentages are by volume unless otherwise stated.

The invention is a process for dehydrating solvents, particularly solvents that are readily miscible with water, and especially ethanol.

The process of the invention can be used to separate essentially any solvent/water solution or mixture. We believe the process of the invention is of particular value in separating solutions in which the organic component is in the range $C_1$-$C_6$, that is, has 1 to 6 carbon atoms, or where the solubility of water in the organic liquid at room temperature and pressure is at least about 5 wt %.

By way of example, the process of the invention is particularly useful for separating water from alcohols, ketones, aldehydes, organic acids and esters, including:
ethanol, particularly bioethanol produced from natural sources ($C_2$)
isopropanol ($C_3$)
butanol ($C_4$)
acetone ($C_3$)
formaldehyde ($C_1$)
ABE.

One or multiple organic compounds may be present in the mixture to be separated. A common example of an organic mixture to be treated is ABE, an acetone-butanol-ethanol mixture produced, for example, by fermentation using clostridium organisms, and used as a source of biobutanol and other valuable chemicals.

The feed stream may contain additional components besides organic solvents and water, such as inorganic salts, fermentation debris and the like. The feed stream may come from any source, and may be subjected to pretreatment, such as filtration, to remove contaminants before it enters the distillation column.

Representative sources of the feedstream include processes that manufacture organic solvents and processes that use organic solvents. Feedstreams that are particularly suited to treatment are those from the manufacture of light alcohols, ketones, aldehydes, organic acids and esters by chemical synthesis or fermentation.

Such manufacturing processes include, but are not limited to, chemical syntheses from petrochemical feedstocks, such as ethylene and propylene; fermentation of sugar-containing feedstocks; saccharification/fermentation of cellulosic and lignocellulosic feedstocks; and conversion of carbonaceous materials to syngas, followed by chemical or biochemical production of the desired solvent.

The solvent and water may be present in any ratio. The process is particularly useful and beneficial, however, in treating streams in which the initial solvent concentration is less than 50 wt %, such as less than 30 wt %, 20 wt %, 15 wt %, 10 wt %, 5 wt % or even less. Such streams are very hard to treat in an energy efficient and cost-effective manner by prior art processes.

The process incorporates two distillation steps in series, operated at different pressures, followed by one or two membrane separation steps.

The invention in a basic embodiment is shown in FIG. 1. It will be appreciated by those of skill in the art that this figure, and the other figures are very simple schematic diagrams, intended to make clear the key aspects of the invention, and that an actual process train will usually include many additional components of a standard type, such as heaters, chillers, condensers, pumps, blowers, other types of separation and/or fractionation equipment, valves, switches, controllers, pressure-, temperature, level- and flow-measuring devices and the like.

In particular, the only sources of heat energy for the first column reboiler are shown as internal process streams. Additional heat energy from conventional sources, such as steam, will often be necessary to heat the reboil stream sufficiently, but these are familiar to those of skill in the art and have been omitted for clarity.

Referring to FIG. 1, feed stream, 101, which is usually a liquid, is passed into first distillation column, 102. In the basic embodiment shown in FIG. 1, the first column takes the form of a stripping column, without a reflux condenser, although the column may optionally be equipped with a reflux system to provide rectification as well as stripping capability.

Energy for the stripping section is provided at least in part by reboiler heat exchanger, 113, in which a portion, 114, of the liquid bottoms stream, 118, is evaporated for return to the column as heated vapor stream, 115.

The column may be operated at any temperature and pressure appropriate to the separation that is to be carried out. For the separation of common organic solvents as listed above, such as ethanol, it is often preferable to operate the column under a partial vacuum and at elevated temperature. For example, the column may be operated at 0.5 bar pressure with the overhead vapor being withdrawn at 70° C. or 80° C.

First overhead vapor stream, 103, is passed from the column to vapor compressor or compression step, 104. The compressor increases the pressure of the first overhead vapor stream to any desired value, typically to a few bar, such as 3 bar or 4 bar. Although power is required to drive the vapor compressor, much of the compression energy can be recovered by heat exchange between the columns as described below.

The process is usually carried out with a mechanical vapor compressor, although any other equivalent methods to achieve a compressed vapor feed to the second column are intended to be within the scope of the invention.

The compressed overhead vapor stream, 105, is enriched in solvent compared with raw feed 101. The concentration of solvent in the column overhead depends on the composition of the raw feed and the operating features of the column. In general, it is preferred to operate the first column as a stripping column to deliver an overhead stream containing about 45-65 wt % solvent, such as about 55 or 60 wt % solvent.

The compressed overhead vapor is passed as feed to the second distillation column, 106, and preferably enters the column at a tray position that matches its composition. In the basic embodiment shown in FIG. 1, the second column takes the form of a rectification column without a reboiler, although the column may optionally be equipped with a reboiler system to provide stripping as well as rectification capability.

Reflux liquid for this column is preferably provided at least in part by heat exchanger, 113, which serves not only as a reboiler for column 102 but also as a reflux condenser for column 106. A portion 116, of the second overhead vapor stream, 107, is condensed for return to the second column as reflux stream, 117. The energy recaptured in this way substantially or completely offsets the energy required to operate the compression step.

FIG. 1 shows the reboil and reflux streams being run directly against one another in heat exchanger 113. It will be apparent to those of skill in the art that circulating a heat transfer medium in the heat exchanger to act as an indirect heat carrier between the two streams would also be possible if desired, and would be substantially functionally equivalent to direct heat exchange in this and all other embodiments.

Additional energy to operate the reboiler is provided as needed by any other means, such as heat exchange against other process streams, or by steam heating.

The second column is operated at a higher pressure than the first column, which pressure is determined by the vapor compressor. Preferably, this pressure is between about 1 and 3 bar. The column produces a bottoms stream, 119, which may be sent to any destination. As this stream typically has a solvent concentration comparable with that of the raw feed, or higher than the raw feed, it is convenient and desirable to recirculate this stream to form part of the feed to the first column, thereby avoiding solvent losses from the process.

Preferably, the pressure and temperature operating conditions of the second column are set to deliver an overhead vapor stream with a solvent concentration of about 70-90 wt % solvent, and most preferably at least about 80 wt % solvent.

If the raw feed to the process is very dilute, such as containing no more than about 5 wt % solvent, it is often convenient, and can result in lower overall energy usage, to operate the second column to achieve a lower overhead concentration, in the range 55-75 wt %, such as about 60 wt %, and to use two membrane separation steps, as explained below.

Overhead vapor that is not sent for reflux is passed as feed stream, 108, to membrane separation step or unit, 109, containing membranes, 110. Optionally, the pressure may be increased by a second compression step, 114, before the vapor is passed to the membrane unit. Splitting the compression between steps 104 and 114 is advantageous in that the total compression energy to operate the process may be much lower, as the second compressor operates on a much smaller vapor stream than the first compressor. For example, the first compressor may raise the pressure of the first overhead stream to only 1.5 bar or 2 bar, and the second compressor may raise the pressure of the second overhead to 3 bar or 4 bar.

A disadvantage of this design, however, is the need for two separate compressors, which adds to the complexity of the equipment.

A driving force for membrane permeation is provided by maintaining the permeate side of the membrane at a lower pressure than the feed side. Lowering the permeate pressure both increases the driving force for transmembrane permeation, increasing transmembrane flux, and increases the pressure ratio, improving the solvent/water separation performance.

The pressure difference and pressure ratio may be increased by using a vacuum pump in the permeate line to pull a vacuum on the permeate side. We have found, however, that simply cooling the permeate stream to condense the stream and create a spontaneous partial vacuum on the permeate side will provide an adequate pressure ratio in most cases, and this is our preferred mode of operation.

Condensation is achieved by cooling, typically by air or water cooling to lower the temperature to below 50° C. By operating in this manner, a pressure of 0.5 bar, 0.1 bar or lower can be reached on the permeate side.

As a typical example, the feed side may be at 3 bar total pressure and the permeate side at 0.5 bar or 0.25 bar pressure, providing a pressure ratio of 6 or 12.

The membranes, 110, may be of any type that provides selectivity in favor of water over the organic solvent. In any membrane separation, the enrichment in the permeate stream of the faster permeating component (by which we mean the concentration of that component in the permeate stream divided by the concentration in the feed) can never be greater than the pressure ratio (by which we mean the total pressure on the feed side divided by the total pressure on the permeate side), irrespective of the membrane selectivity.

The membrane separation step typically operates at a modest pressure ratio, such as less than 30, so a very high selectivity is not needed for this step. In general, the preferred membrane selectivity should be less than 100, and most preferably in the range of 10-100, such as up to about 20, 30, 50 or 60.

A selectivity higher than 100 can even be disadvantageous, as this implies a very low permeance for the slower permeating component, that is, the solvent. The membrane area requirements for the separation are controlled by the slower permeating component, so a very slow permeation rate for the solvent can lead to a very high membrane area requirement.

Subject to the above-preference for membranes of moderate selectivity, suitable membranes that can be used may be found within several classes, including polymeric membranes and inorganic membranes.

Representative water-selective membrane types include, but are not limited to, polymeric membranes having a hydrophilic selective layer, such as polyvinyl alcohol (PVA) or cellulose acetate, or having a hydrophobic selective layer of the type taught in U.S. pending application Ser. No. 11/897,675, copending with the present application.

Yet other suitable membranes include chitosan membranes, and ion-exchange membranes, such as Nafion® membranes.

Inorganic membranes comprising hydrophilic materials may also be used as dehydration membranes. Such membranes include amorphous silica membranes and membranes including a water permeating zeolite layer, such as ZSM-5. Various types of inorganic membranes may be purchased from Mitsui and Company (USA) of New York, Isotronics of Paradise Valley, Ariz., Sulzer Chemtech Membrane Systems, based in Heinitz, Germany, and Pervatech BV of Enter, Netherlands.

The membrane separation unit can include a single membrane module or a bank or array of membrane modules.

Water permeates the membrane preferentially, to form water-enriched, solvent-depleted permeate stream, 112, in vapor form. This stream is returned within the process, either to the first distillation column as indicated generally by dashed line A, or to the second distillation column as indicated generally by dashed line B. Recycle of the permeate stream within the process increases solvent recovery.

The permeate may be returned as vapor or as liquid to either column, although for simplicity it is indicated at A as vapor returned to the lower part of the column, and at B as liquid returned to the upper part of the column.

Returning stream 112 as vapor recovers the latent heat content and usually results in a lower energy process overall. Cooling and condensing the stream, however, reduces the permeate pressure. Although the latent heat is lost, the increased pressure ratio across the membrane improves performance and reduces membrane area.

In embodiments such as that of FIG. 1, where only one membrane separation step is used, it is preferred to condense the permeate stream, to increase transmembrane pressure ratio and pressure difference, and to return the condensate to the second column.

The residue stream, 111, from the membrane separation step is enriched in solvent compared with the feed stream, and is withdrawn as the dehydrated product of the process. Preferably, this stream contains at least 90 wt % solvent, and more preferably at least 95 wt % solvent. Most preferably, the product is dehydrated to at least 98 wt % or 99 wt % solvent, or better.

The flow rate and composition of the residue stream depend on the operating features of the membrane separation step, such as pressure difference, pressure ratio, membrane selectivity and permeance, and membrane area. To achieve the preferred results, the membrane should typically provide a water permeance of at least about 1,000 gpu, and most preferably at least about 2,000 gpu, and a selectivity of at least 20, and preferably between 20 and 100, and the step should be operated at a pressure ratio of at least about 5 or 6.

FIG. 1 shows the product residue stream as simply being withdrawn from the process. However, additional heat recovery can be obtained in the process by condensing the dehydrated solvent product vapor stream. Preferably, the stream is cooled by heat exchange against the reboil stream for the first column, the incoming raw feed, or both, as discussed in more detail below.

If greater purity is needed than can conveniently be obtained using one membrane separation step, one or more additional membrane steps may be used to dehydrate the residue stream further. Alternatively, the residue stream can be passed to other non-membrane treatments.

Figure 2:
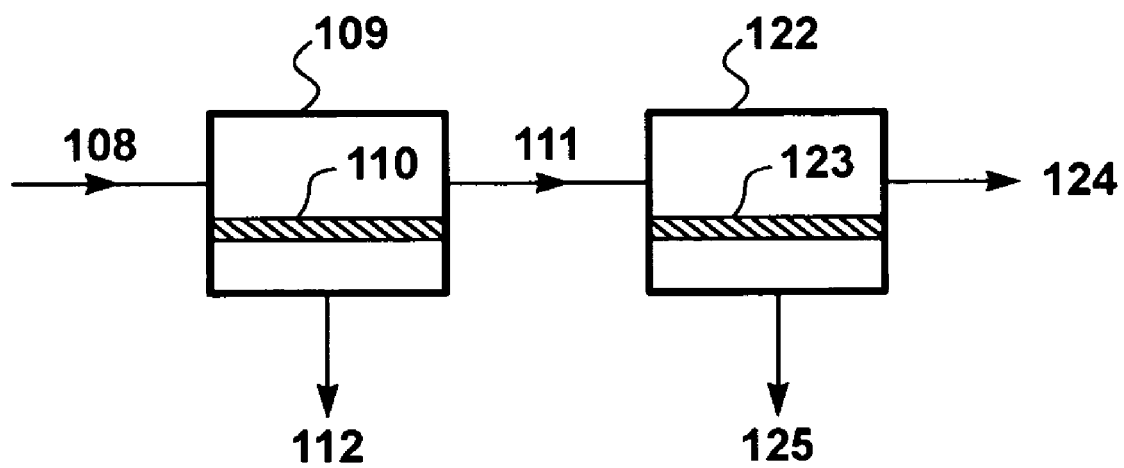
FIG. 2 is a schematic drawing indicating the positioning of a second membrane separation step after the step shown in FIG. 1.

FIG. 2 indicates a process configuration in which two membrane steps are used in series. Like elements are numbered as in FIG. 1. This type of process design is particularly useful in treating very dilute raw feed streams, such as those containing 5 wt % or less of solvent.

In this embodiment, first residue stream, 111, is passed as feed in vapor form to the second membrane separation unit, 122, containing membranes, 123.

The choices of membrane for the second step are similar to those for the first step. Optionally, the membranes used in the second unit may be different from those used in the first unit.

Likewise, the feed and permeate operating pressures and temperatures for the second membrane separation step may be the same or different from those for the first membrane separation step. In this design, the second membrane separation step delivers the treated product stream, so it is preferred to operate this step with a partial vacuum on the permeate side to increase pressure ratio, as described above for the single membrane separation step in the FIG. 1 embodiment.

As with the FIG. 1 configuration, a vacuum pump may be used in the second permeate line to pull a vacuum on the permeate side. A better option is to cool and condense the second permeate stream, 125, as described above. Stream 125, in condensed form, is preferably returned to the second column, where it contributes to the reflux for the column.

In this embodiment, the first membrane separation step acts as an intermediary separation between the second column and the second membrane step. As a result, the performance requirements for the first membrane step are less constrained than those for the second step, and the first step may operate at a lower pressure ratio than the second. In this case, first permeate stream, 112, may simply be returned as a vapor to the first column.

If the second membrane separation step is operated at a higher pressure ratio than the first membrane separation step, this step is less pressure ratio limited than the first step. A higher selectivity may then be beneficial, and preferred membranes for the second step have selectivities up to 200 or 250.

The residue stream flows across the feed side of the second membrane unit. The second step produces a second residue vapor stream, 124, which is withdrawn as a dehydrated solvent product.

As mentioned for the FIG. 1 configuration, additional heat recovery can be obtained in the process by condensing the dehydrated solvent product vapor stream against another process stream.

Figure 3:
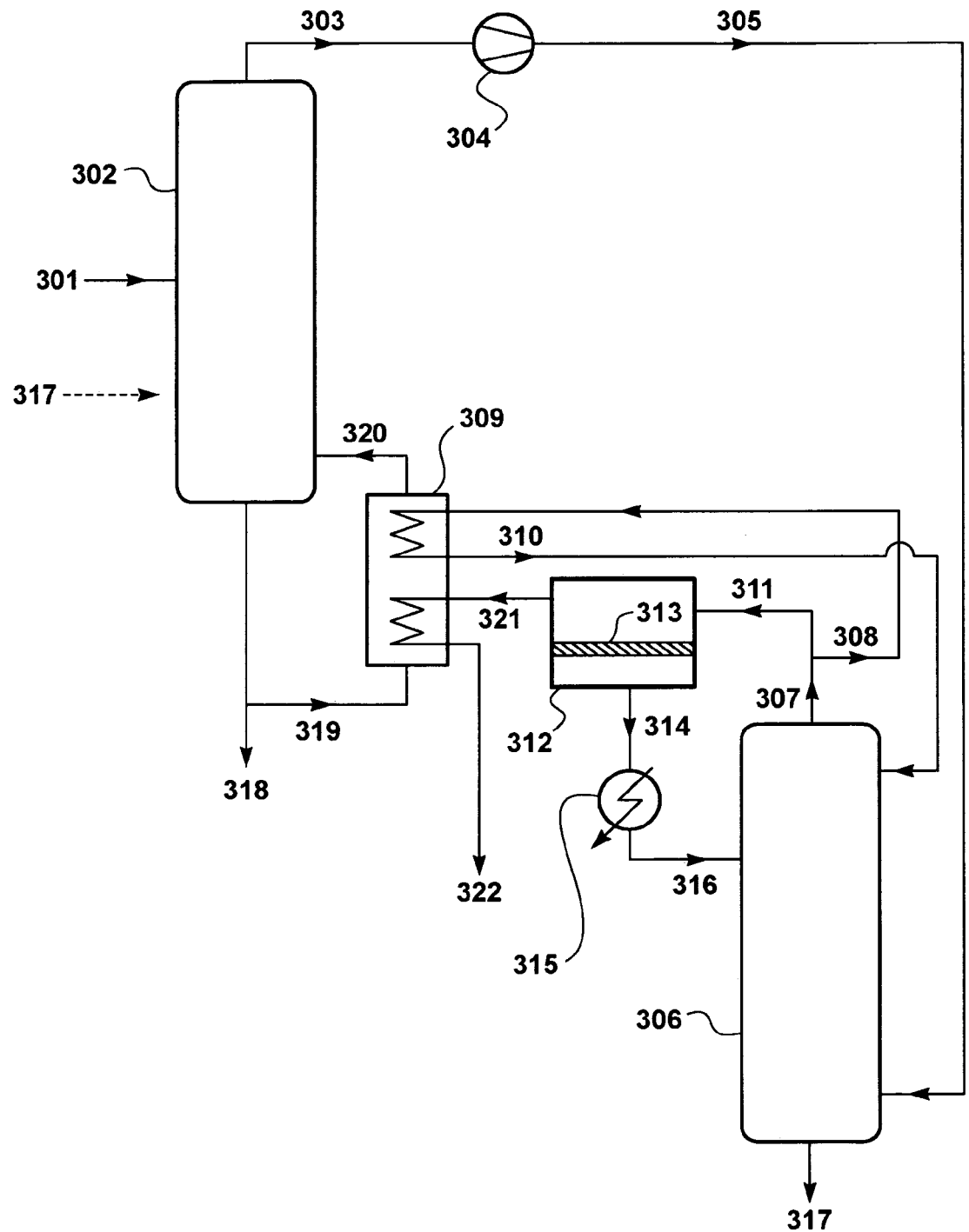
FIG. 3 is a schematic drawing showing a preferred embodiment of the invention in which the membrane permeate stream is condensed and returned to the second column, and in which the product residue stream is condensed by heat exchange in the reboiler of the first column.

A preferred embodiment of the invention in which the reboiler system includes heat exchange against the residue product stream is shown in FIG. 3. Unless explicitly stated otherwise, operating preferences for this embodiment are the same as for FIG. 1.

Referring to FIG. 3, feed stream, 301, is passed into first distillation column, 302, which may take the form of a stripping column, as shown, or may be equipped in addition with a reflux condenser to provide rectification as well as stripping capability.

Energy for the stripping section is provided at least in part by reboiler heat exchanger, 309, in which a portion, 319, of the liquid bottoms stream, 318, is evaporated for return to the column as heated vapor stream, 320.

First overhead vapor stream, 303, is passed from the column to vapor compressor or compression step, 304. The compressed overhead vapor stream, 305, is passed as feed to the second distillation column, 306, which may be equipped only with a reflux condenser, as shown, or may also include a reboiler system to provide stripping as well as rectification capability.

Reflux liquid for this column is provided at least in part by heat exchanger, 309, which preferably serves not only as a reboiler for column 302 but also as a reflux condenser for column 306. A portion 308, of the second overhead vapor stream, 307, is condensed for return to the second column as reflux stream, 310.

Bottoms stream, 317, is withdrawn from the column and may be recirculated to the first column, as indicated by the dashed lines, or sent to any other destination.

Overhead vapor that is not sent for reflux is passed as feed stream, 311, to membrane separation step or unit, 312, containing membranes, 313. The permeate side of the membranes is maintained at a lower pressure than the feed side by condensing the permeate stream, 314, in condenser, 315. The condensed permeate stream, 316, is returned to the second column.

The membrane separation step also yields dehydrated residue product stream, 321, which is passed into the reboiler/reflux condenser, 309, where it is condensed to form liquid product stream, 322. Optionally, the residue stream may be used in addition to warm the incoming raw feed stream, 301, before it is discharged from the process.

Figure 4:
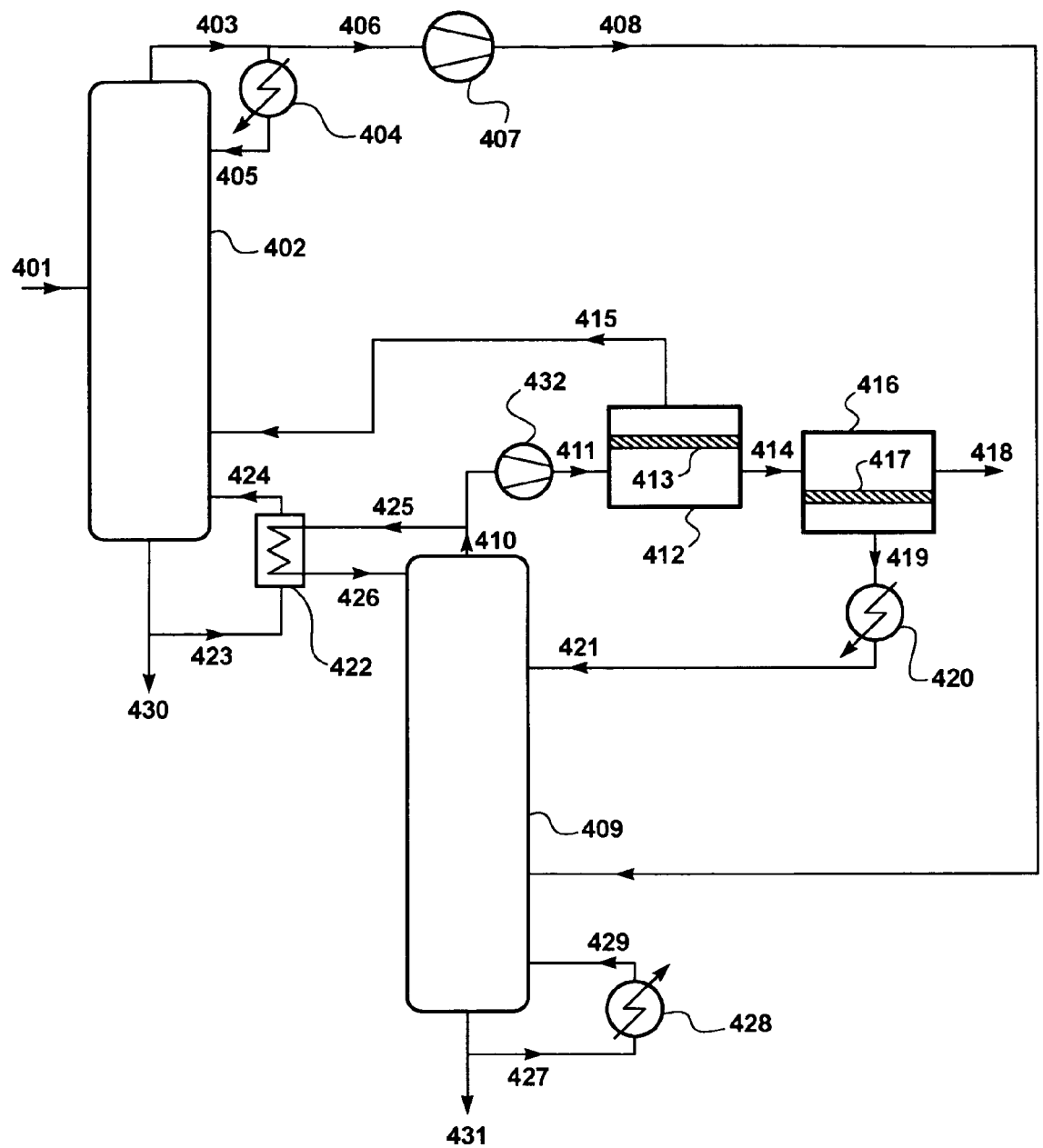
FIG. 4 is a schematic drawing showing an embodiment of the invention in which two membrane separation steps are used, and in which the first permeate stream is returned as vapor to the first column and the second permeate stream is condensed and returned as reflux liquid to the second column.

A preferred embodiment of the invention using two membrane separation steps is shown in FIG. 4. Such a configuration is especially useful in treating raw feed streams that contain less than 5 wt % solvent, for example. As with FIG. 3, operating preferences for this embodiment are the same as for FIG. 1 unless stated otherwise.

For illustrative purposes, both columns are shown as having both stripping and rectification capability in FIG. 4. However, just as in the embodiments having only one membrane separation step, the basic requirements for the columns in the two-membrane-step embodiments are that the first column have at least stripping capability and the second column have rectification capability.

Referring to FIG. 4, feed stream, 401, is passed into first distillation column, 402. In the embodiment shown, the column is equipped with a reflux condenser, 404, in addition to a reboiler heat exchanger, 422. In the reflux condenser, a portion, 405 of the column overhead is condensed for return to the column as a reflux stream. In the reboiler, a portion, 423, of the liquid bottoms stream, 430, is evaporated for return to the column as heated vapor stripping stream, 424. As with the other embodiments, the reboiler heat supply may be supplemented by heat exchange against other process streams, or by steam heating or the like.

Rectified overhead stream, 406, is passed from the column to vapor compressor or compression step, 407. The compressed overhead vapor stream, 408, is passed as feed to the second distillation column, 409, which is equipped with a reboiler, 428, in which a portion, 427, of bottoms stream, 431, is heated to produce vapor stream, 429, for return to the column.

Reflux liquid for this column is provided at least in part by heat exchanger, 422, which serves not only as a reboiler for column 402 but also as a reflux condenser for column 409. A portion, 425, of the second overhead vapor stream, 410, is condensed for return to the second column as reflux stream, 426.

Overhead vapor that is not sent for reflux is compressed in second compression step, 432, and passed as feed stream, 411, to membrane separation step or unit, 412, containing membranes, 413. This step separates the overhead stream into first residue stream, 414, and first permeate stream, 415. In this embodiment, it is preferred to simply return stream 415 as a vapor to the first column.

First residue stream 414 is withdrawn from membrane unit 412 and passed as feed in vapor form to the second membrane separation unit, 416, containing membranes, 417. This unit produces second residue stream, 418, which is the dehydrated product of the process, and second permeate stream, 419, which is condensed in condenser, 420, and returned as condensed permeate stream, 421, to the second column.

As with the embodiments described previously, additional heat recovery can be obtained by condensing stream 418 by heat exchange in the reboiler system or against the incoming feed, or elsewhere within the process.

In the designs described above, all of the raw feed stream enters the process at the first distillation column. It is also within the scope of the invention to split the raw feed, so that one portion is sent to the first column and another portion is sent to the second column. This type of embodiment can provide processes with very low total energy usage for the purification of bioethanol for example.

If a split feed process is used, at least about 50% of the feed is usually directed to the first column, and it is preferred to split the feed so as to send between about 65-85% of the feed to the first column, as we have discovered that this range offers the best overall energy efficiency for the process. Most preferably, 70-80% of the feed is directed to the first column, and the remaining 30-20% to the second.

It is also possible to use the process of the invention to treat two different feed mixtures simultaneously. Such an embodiment can be useful, for example, if two feeds from different sources, or having different concentrations of solvent, are to be treated.

Figure 5:
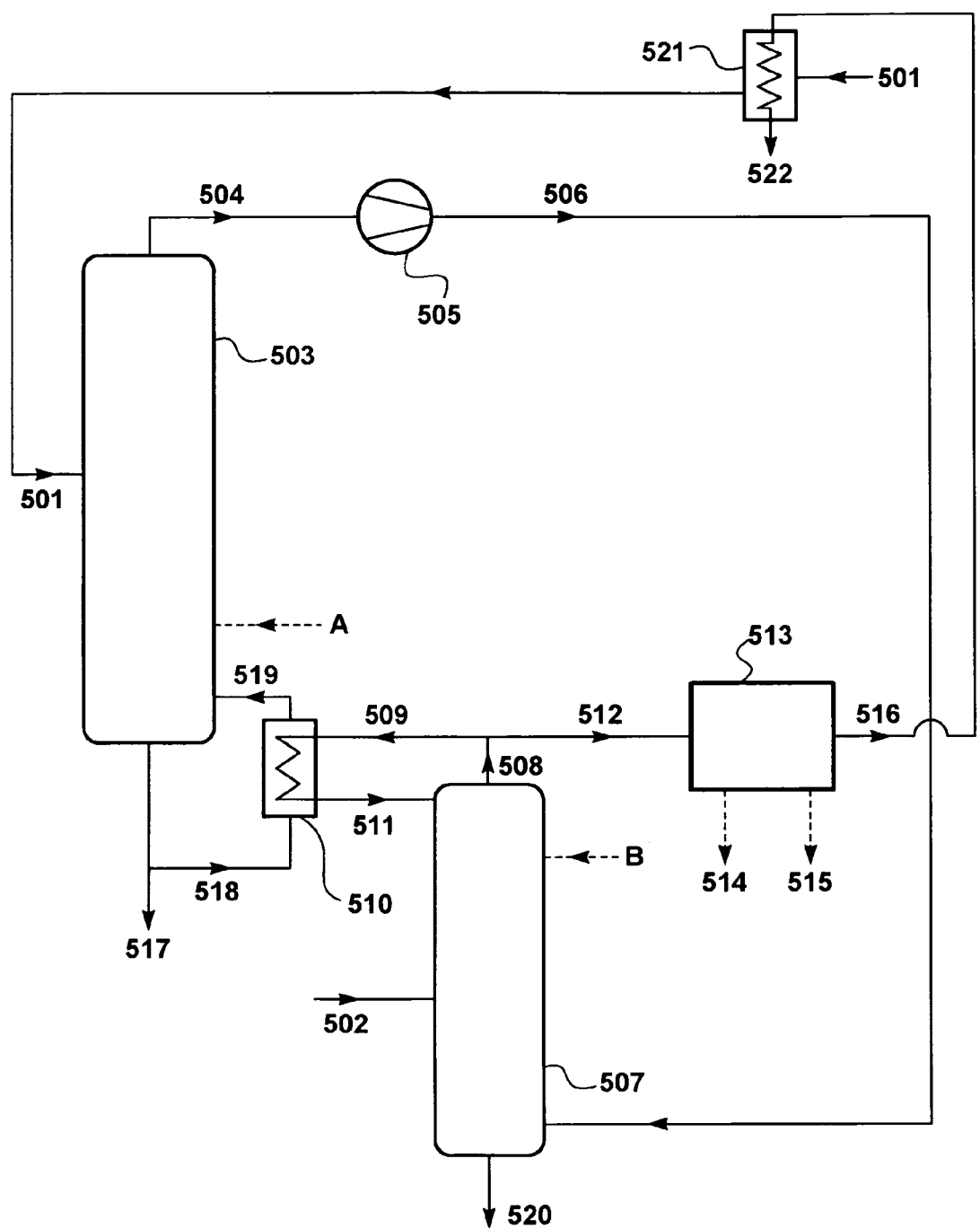
FIG. 5 is a schematic drawing showing an embodiment of the invention in which feed is introduced to both the first and second columns.

FIG. 5 illustrates an embodiment of the invention to treat either a single split feed, or two different feeds. As before, options and preferences are the same as for FIG. 1, unless stated to be otherwise. Referring to FIG. 5, first feed stream, 501, enters the process and passes through optional heat exchanger, 521, where it is warmed against product stream, 516, and then passed into first distillation column, 503.

Second feed stream, 502, which may optionally also be warmed against the product stream, is passed into second distillation column, 507. As mentioned above the feeds may be from the same or different sources, and may be of the same or different compositions.

As one example, both feeds may be from the fermentation of corn to ethanol, and may each contain about 12 wt % ethanol.

As another example, one feed may be from the fermentation of corn to ethanol, and may contain proteins and other biological matter in addition to ethanol and water. If this feed were to be sent directly to the high-pressure column, these materials could deposit out as solids in the column, fouling the trays and impairing column performance. In this case, this feed cannot be split (unless previously treated to remove the contaminants), and is sent entirely to the first column. If the plant also processes cellulosic materials, such as corn stover, however, the raw fermentation product from the cellulosic feed is relatively free of proteins and fats, although it may typically contain only about 5 wt % ethanol. This product can be sent as the second feed directly to the high-pressure column.

Energy for operating the first column is provided at least in part by reboiler heat exchanger, 510, in which a portion, 518, of the liquid bottoms stream, 517, is evaporated for return to the column as heated vapor stream, 519.

First overhead vapor stream, 504, is passed from the column to vapor compressor or compression step, 505, and the resulting compressed overhead vapor stream, 506, is passed as feed to the second distillation column, 507.

Reflux liquid for this column is provided at least in part by heat exchanger, 510, which serves not only as a reboiler for column 502 but also as a reflux condenser for column 507. A portion, 509, of the second overhead vapor stream, 508, is condensed for return to the second column as reflux stream, 511.

The column produces a bottoms stream, 520, which may be recirculated or discharged.

Overhead vapor that is not sent for reflux is passed as feed stream, 512, to the membrane separation step(s), indicated by box, 513. The membrane separation may be carried out in one or two steps, as already explained with respect to the other embodiments. Product residue stream, 516, is withdrawn from the membrane separation step(s), and is condensed to form liquid product stream, 522, in heat exchanger 521.

Depending on whether one or two membrane separation steps are used, one or two permeate streams, 514 and 515, are produced, and may be recirculated to the first or second column as indicated by dashed arrows A and B. If one membrane separation step is used, the permeate stream is preferably condensed and returned to the second column; if two steps are used, it is preferred to send the first permeate back as vapor to the first column and the second permeate back as condensate to the second column.

In another aspect, the invention is a process for producing light alcohols by fermentation, using a combination of steps including fermentation, distillation at two different pressures, and membrane separation. The invention in this is illustrated in FIG. 7, where, once again options and preferences are the same as for FIG. 1, unless stated otherwise.

Figure 7:
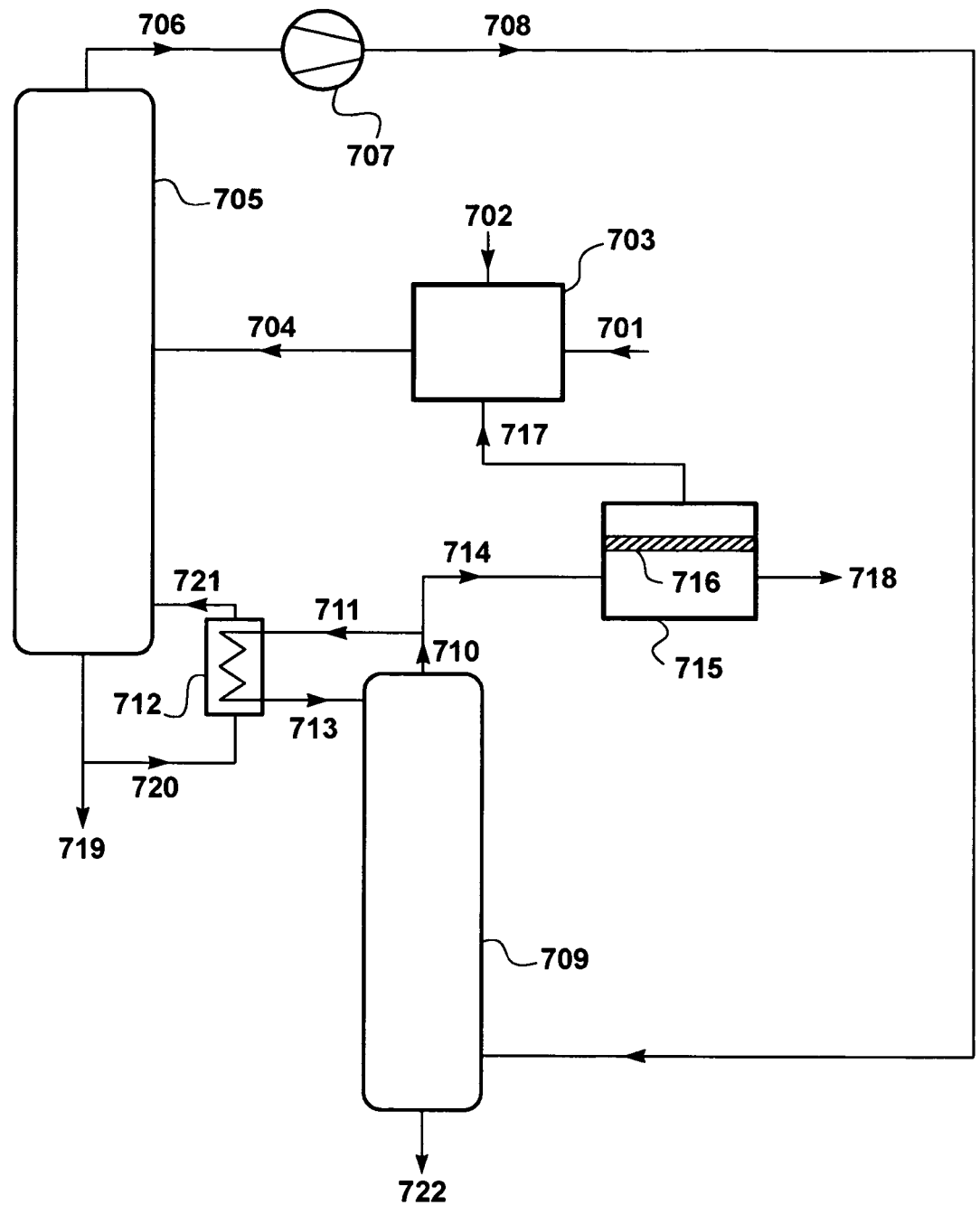
FIG. 7 is a schematic drawing showing an embodiment of the invention in an aspect that relates to the production of a light alcohol.

Referring to FIG. 7, a feedstock, 701, and a fermentation agent, 702, enter fermentation step or vessel, 703. The feedstock may be any material that contains a fermentable sugar.

Preferred sources of feedstock include waste materials that contain sugar, starch, cellulosic or other substances that can be converted to sugar. These types of waste are diverse, and include: food-processing wastes, such as cheese whey; other agricultural wastes, such as grape skins; and cellulosic wastes, such as corn stover or wood waste. Other examples of feedstocks include biomass that may be grown specifically as a source of raw material for alcohol production, such as cereal grains, grasses, sugarcane and root crops.

The fermentation step may be carried out using any reaction that can convert a sugar to an alcohol. Preferably the reaction is the commonplace enzymatic reaction using yeast to ferment a six-carbon sugar to ethanol. Other representative fermentation reactions include the use of clostridium organisms to produce ABE (acetone-butanol-ethanol). The step may be carried out in any type of batch or continuous mode.

If the source material itself does not contain adequate quantities of sugar, but may be treated to form sugars, the invention may include one or more additional steps to carry out appropriate treatment, such as to convert starch or cellulose to sugar, or to break down lignin and then convert exposed cellulose. These steps may be carried out as pretreatment before the material enters the fermentation vessel, or may be performed simultaneously with the fermentation step.

The invention may include one or more filtration steps between the fermentation step and the first membrane separation step, to recover yeast cells, to remove other suspended solid matter that might foul the membranes in the membrane separation step, to remove dissolved nutrients, salts or excess sugar, or otherwise to prepare the feed to the membrane separation step. Depending on the materials to be removed, this filtration step can optionally include one or more of microfiltration, ultrafiltration, nanofiltration or reverse osmosis.

Stream, 704, containing light alcohol and water, is passed from the fermentation step or unit to first distillation step or column, 705. Energy for operating the first column is provided at least in part by reboiler heat exchanger, 712, in which a portion, 720, of the liquid bottoms stream, 719, is evaporated for return to the column as heated vapor stream, 721.

First overhead vapor stream, 706, is passed from the column to vapor compressor or compression step, 707, and the resulting compressed overhead vapor stream, 708, is passed as feed to the second distillation column, 709.

Reflux liquid for this column is provided at least in part by heat exchanger, 712, which serves not only as a reboiler for column 705 but also as a reflux condenser for column 709. A portion, 711, of the second overhead vapor stream, 710, is condensed for return to the second column as reflux stream, 713.

The column produces a bottoms stream, 722, which may be recirculated or discharged.

Overhead vapor that is not sent for reflux is passed as feed stream, 714, to membrane separation step or unit, 715, containing membranes 716. Dehydrated alcohol product residue stream, 718, is withdrawn from the membrane separation steps, and may optionally be condensed in heat exchanger 712 or elsewhere within the process as desired for additional heat recovery.

In this case, the permeate stream, 717, from the membrane separation step is recirculated to the fermenter, 703.

Figure 8:
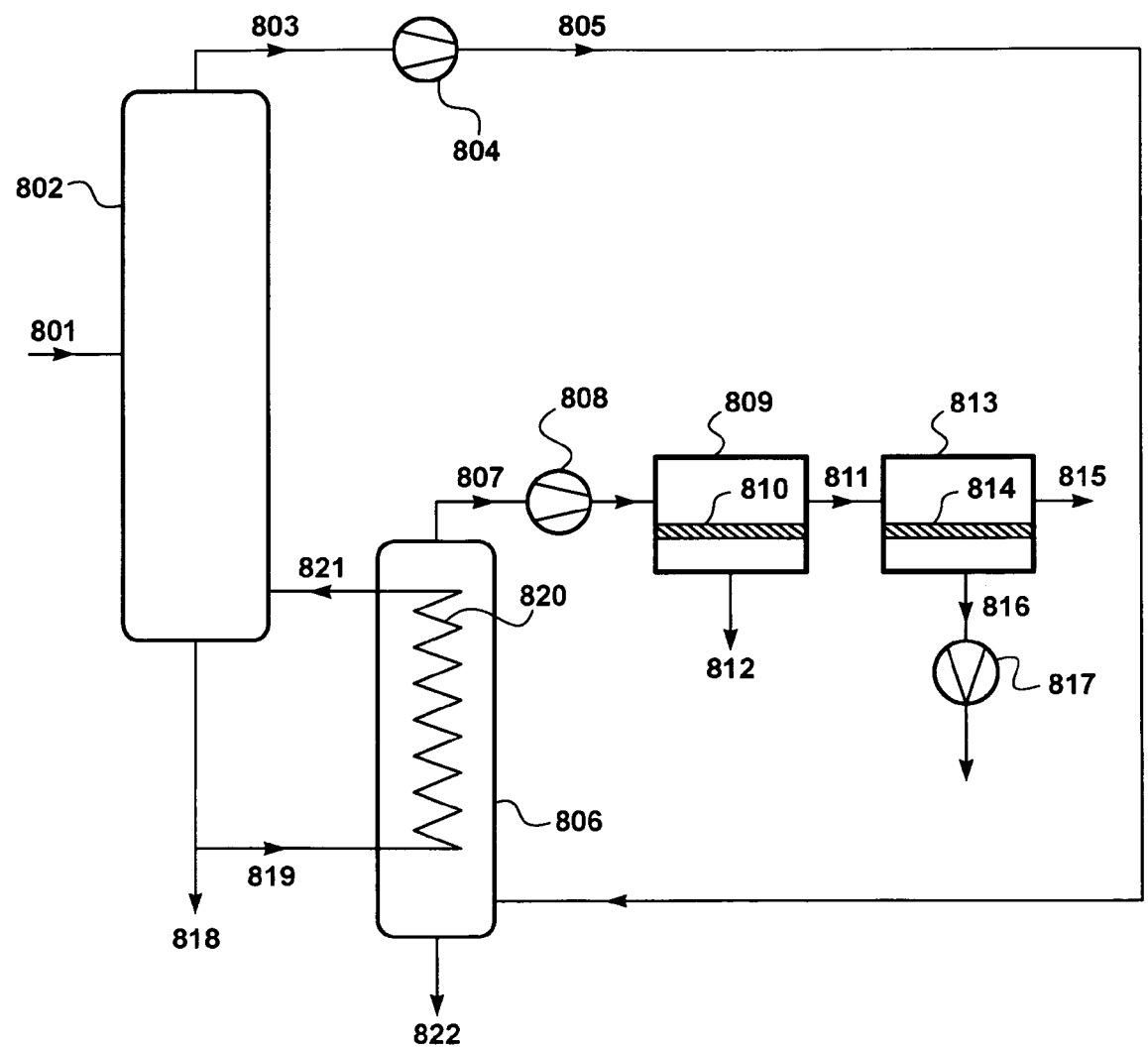
FIG. 8 is a schematic drawing showing an embodiment of the invention in which heat exchange between the columns takes place within the second column.

The invention in the variant in which heat exchange between the columns takes place within the second column is shown in FIG. 8. Referring to this figure, feed stream, 801, is passed into first distillation column, 802.

Overhead stream, 803, is passed from the column to vapor compressor or compression step, 804. The compressed overhead vapor stream, 805, is passed as feed to the second column, 806. This column does not have an external reflux condenser, but rather takes the form of a simple shell-and-tube dephlegmator, with internal heat exchange, 820. Vapor 805 enter the column and flows upward on the shell side of the heat exchanger; reboil liquid stream, 819, from the first column flows in the tubes and passes out of the second column as heated reboil stream, 821. This stream can optionally be subjected to additional heating from other process streams or by steam, for example, before being passed back to the first column as hot vapor.

Although the figure shows the dephlegmator column operating solely as a vertical shell-and-tube heat exchanger, it will be apparent that other types of dephlegmator design, such as are described in U.S. Pat. No. 6,755,975 for example, could be used in this embodiment, and are within the scope of the invention.

Overhead vapor, 807, from the second column is compressed in optional compression step, 808, and passes as feed to membrane separation step or unit, 809, containing membranes, 810. This step separates the overhead stream into first residue stream, 811, and first permeate stream, 812. The permeate stream may be returned as vapor or liquid to either column as described previously.

First residue stream 811 is withdrawn from membrane unit 809 and passed as feed in vapor form to the second membrane separation unit, 813, containing membranes, 814. This unit produces a second residue stream, 815, which is the dehydrated product of the process, and a second permeate stream, 816.

For representative, non-limiting purposes, this embodiment is shown in the case in which a vacuum pump, 817, is used on the permeate side of the second membrane unit to increase the driving force and pressure ratio across membranes 814. The second permeate may be returned as vapor or liquid to either column after passing through the pump.

Bottoms streams, 818 and 822, are withdrawn from the columns. Optionally, bottoms stream 822 may be recirculated to the first column.

The invention is now further described by the following examples, which are intended to be illustrative of the invention, but are not intended to limit the scope or underlying principles in any way.

EXAMPLES

Example 1

A computer calculation was performed with a modeling program, ChemCad 5.5.1 (ChemStations, Inc., Houston, Tex.) to illustrate the process of the invention in the embodiment shown in FIG. 3, except that the product stream, 321, was assumed to be condensed by heat exchange against incoming feed, 301.

The calculation assumed that the feed composition was 11.5% ethanol and 88.5% water, representative of a raw feed from a bioethanol manufacturing process. The process was assumed to use a stripping column, having 15 stripping stages and a rectification column, having 15 stages also. The columns were assumed to operate at 0.5 bar and 3 bar respectively. The bottom stream, 317, from the second column was assumed to be recirculated to the first column.

The process was configured to provide a rectified overhead stream, 311, containing about 85 wt % ethanol, and a dehydrated product stream, 322, containing 99.7 wt % ethanol. The membranes were assumed to have a selectivity for water over ethanol of about 30 and a water permeance of about 2,000 gpu, as is consistent with the membranes described in co-owned U.S. Pat. No. 8,002,874, issued Aug. 23, 2011, to Huang et al., and co-owned and copending U.S. application Ser. No. 11/897,675, for example. The results of the calculations are summarized in Table 1.

TABLE 1

| | Stream | | | | | |
|---|---|---|---|---|---|---|
| | 301 (Feed) | 305 | 311 (Rectified overhead) | 314 | 317 | 318 | 322 (Product ethanol) |
| Flow (kg/h) | 165,000 | 34,722 | 27,470 | 8,584 | 15,837 | 146,113 | 18,886 |
| Temp (° C.) | 37 | 191 | 110 | 111 | 121 | 81 | 54 |
| Pressure (bar) | 1.0 | 3.0 | 3.0 | 0.1 | 3.0 | 0.5 | 3.0 |
| Component | | | | | | | |
| Water | 88.5 | 38.0 | 15.0 | 47.3 | 82.8 | 99.9 | 0.3 |
| Ethanol | 11.5 | 62.0 | 85.0 | 52.7 | 17.2 | 0.1 | 99.7 |

The energy consumption of the compressor was calculated at 1,960 kW-h. For this and the other examples, we assumed that 1 kW-h is equivalent to 10,000 Btu/h, which gives an energy input for the compressor of 19.6 million Btu/h. This conversion effectively multiplies the energy consumption of the compressor by a factor of 3 to take into account the inefficiency of converting heat to electric power.

The process was calculated to use total energy of 53.5 million Btu/h, and 4,340 m² of membrane area.

Example 2

A computer calculation was performed using the same basic assumptions as for Example 1. In this case, however, it was assumed that the second column is also equipped with a small reboiler, so that the bottoms stream from this column is essentially pure water and is discharged, not recirculated. The results of the calculations are summarized in Table 2.

TABLE 2

| | Stream | | | | | |
|---|---|---|---|---|---|---|
| | 301 (Feed) | 305 | 311 (Rectified overhead) | 314 | 317 | 318 | 322 (Product ethanol) |
| Flow (kg/h) | 165,000 | 30,120 | 27,473 | 8,584 | 11,232 | 134,880 | 18,888 |
| Temp (° C.) | 37 | 190 | 113 | 111 | 134 | 81 | 47 |
| Pressure (bar) | 1.0 | 3.0 | 3.0 | 0.1 | 3.0 | 0.5 | 3.0 |
| Component | | | | | | | |
| Water | 88.5 | 37.5 | 15.0 | 47.3 | 99.9 | 99.9 | 0.3 |
| Ethanol | 11.5 | 62.5 | 85.0 | 52.7 | 0.1 | 0.1 | 99.7 |

The addition of the small reboiler made almost no difference to the total energy usage, which was 53.7 million Btu/h.

Example 3

A computer calculation was performed using the same basic assumptions as for Example 1. In this case, however, it was assumed that the first column is equipped with a reflux condenser to provide rectification in the column. The results of the calculations are summarized in Table 3.

TABLE 3

| | Stream | | | | | |
|---|---|---|---|---|---|---|
| | 301 (Feed) | 305 | 311 (Rectified overhead) | 314 | 317 | 318 | 322 (Product ethanol) |
| Flow (kg/h) | 165,000 | 40,966 | 27,487 | 8,589 | 22,071 | 146,109 | 18,898 |
| Temp (° C.) | 37 | 142 | 110 | 111 | 111 | 81 | 55 |
| Pressure (bar) | 1.0 | 3.0 | 3.0 | 0.1 | 3.0 | 0.5 | 3.0 |
| Component | | | | | | | |
| Water | 88.5 | 20.0 | 15.0 | 47.3 | 36.9 | 99.9 | 0.3 |
| Ethanol | 11.5 | 80.0 | 85.0 | 52.7 | 63.1 | 0.1 | 99.7 |

The addition of the reflux condenser increased the total energy usage of the process to 69.0 million Btu/h, although the amount of high purity ethanol recovered increased very slightly.

Example 4

A computer calculation was performed combining the assumptions of Examples 2 and 3. That is, we assumed that a reflux condenser was added to the top of the first column and a reboiler was added to the bottom of the second column, so that the bottoms stream was discharged, not recirculated. The results of the calculations are summarized in Table 4.

TABLE 4

| | Stream | | | | | |
|---|---|---|---|---|---|---|
| | 301 (Feed) | 305 | 311 (Rectified overhead) | 314 | 317 | 318 | 322 (Product ethanol) |
| Flow (kg/h) | 165,000 | 23,541 | 27,473 | 8,584 | 4,653 | 141,458 | 18,888 |
| Temp (° C.) | 37 | 142 | 113 | 111 | 134 | 81 | 47 |
| Pressure (bar) | 1.0 | 3.0 | 3.0 | 0.1 | 3.0 | 0.5 | 3.0 |
| Component | | | | | | | |
| Water | 88.5 | 20.0 | 15.0 | 47.3 | 99.9 | 99.9 | 0.3 |
| Ethanol | 11.5 | 80.0 | 85.0 | 52.7 | 0.1 | 0.1 | 99.7 |

The total energy usage of the process was 63.0 million Btu/h.

Example 5

The total energy usage and the energy usage for the compressor were compared for Examples 1 through 4. The data are shown in Table 5. The membrane area used in each case is the same as in Example 1, 4,340 m$^2$, because all processes produce a rectified overhead stream of about the same volume containing the same concentration of ethanol (85 wt %).

TABLE 5

| Example No. | Total Energy (MMBtu/h) | Compressor energy (MMBtu/h) |
|---|---|---|
| 1 | 53.5 | 19.6 |
| 2 | 53.7 | 16.9 |
| 3 | 69 | 11.0 |
| 4 | 63 | 6.40 |

As can be seen, the design of Example 1, using a stripping column without rectification followed by a rectification column without a reboiler, uses the least energy overall. The lowest energy requirement for the compressor is provided by the design of Example 4.

Example 6

A computer calculation was performed using the same basic assumptions as for Example 1. In this case, however, the process differed slightly from that of FIG. 3 in that the membrane permeate was assumed to be sent back to the first column in vapor form, rather than condensed and sent to the second column. The results of the calculations are summarized in Table 6.

TABLE 6

| | Stream | | | | | | |
|---|---|---|---|---|---|---|---|
| | 301 (Feed) | 305 | 311 (Rectified overhead) | 314 | 317 | 318 | 322 (Product ethanol) |
| Flow (kg/h) | 165,000 | 39,958 | 27,473 | 8,585 | 12,484 | 146,118 | 18,888 |
| Temp (° C.) | 37 | 187 | 110 | 111 | 120 | 81 | 91 |
| Pressure (bar) | 1.0 | 3.0 | 3.0 | 0.1 | 3.0 | 0.5 | 3.0 |
| | | | Component | | | | |
| Water | 88.5 | 35.5 | 15.0 | 47.3 | 80.5 | 99.9 | 0.3 |
| Ethanol | 11.5 | 64.5 | 85.0 | 52.7 | 19.5 | 0.1 | 99.7 |

The total energy usage for the process was calculated to be only 55.0 million Btu/h, but the energy to operate the compressor was calculated to be high, at 21.9 million Btu/h.

Example 7

A computer calculation was performed using the same basic assumptions as in Example 1, using one column having only stripping capability and one having only reflux. In this case, however, two membrane separation steps in series were used, as in the embodiment of FIG. 4. Both steps were assumed to use membranes providing a selectivity of about 30 and water permeance of 2,000 gpu.

The results of the calculations are summarized in Table 7.

TABLE 7

| | Stream | | | | | | |
|---|---|---|---|---|---|---|---|
| | 401 (Feed) | 408 | 411 (Rectified overhead) | 415 | 418 (Product ethanol) | 419 | 430 | 431 |
| Flow (kg/h) | 165,000 | 35,614 | 27,953 | 2,512 | 18,889 | 6,550 | 146,118 | 14,213 |
| Temp (° C.) | 37 | 191 | 110 | 112 | 109 | 110 | 81 | 121 |
| Pressure (bar) | 1.0 | 3.0 | 3.0 | 0.5 | 3.0 | 0.1 | 0.5 | 3.0 |
| | | | Component | | | | |
| Water | 88.5 | 37.6 | 15.0 | 66.3 | 0.3 | 37.7 | 99.9 | 82.7 |
| Ethanol | 11.5 | 62.4 | 85.0 | 33.7 | 99.7 | 62.3 | 0.1 | 17.3 |

The total energy usage for the process was calculated to be only 49.6 million Btu/h, but the energy to operate the compressor was calculated to be high, at 20.1 million Btu/h. The total membrane area used increased to 4,850 m².

Example 8

Figure 6:
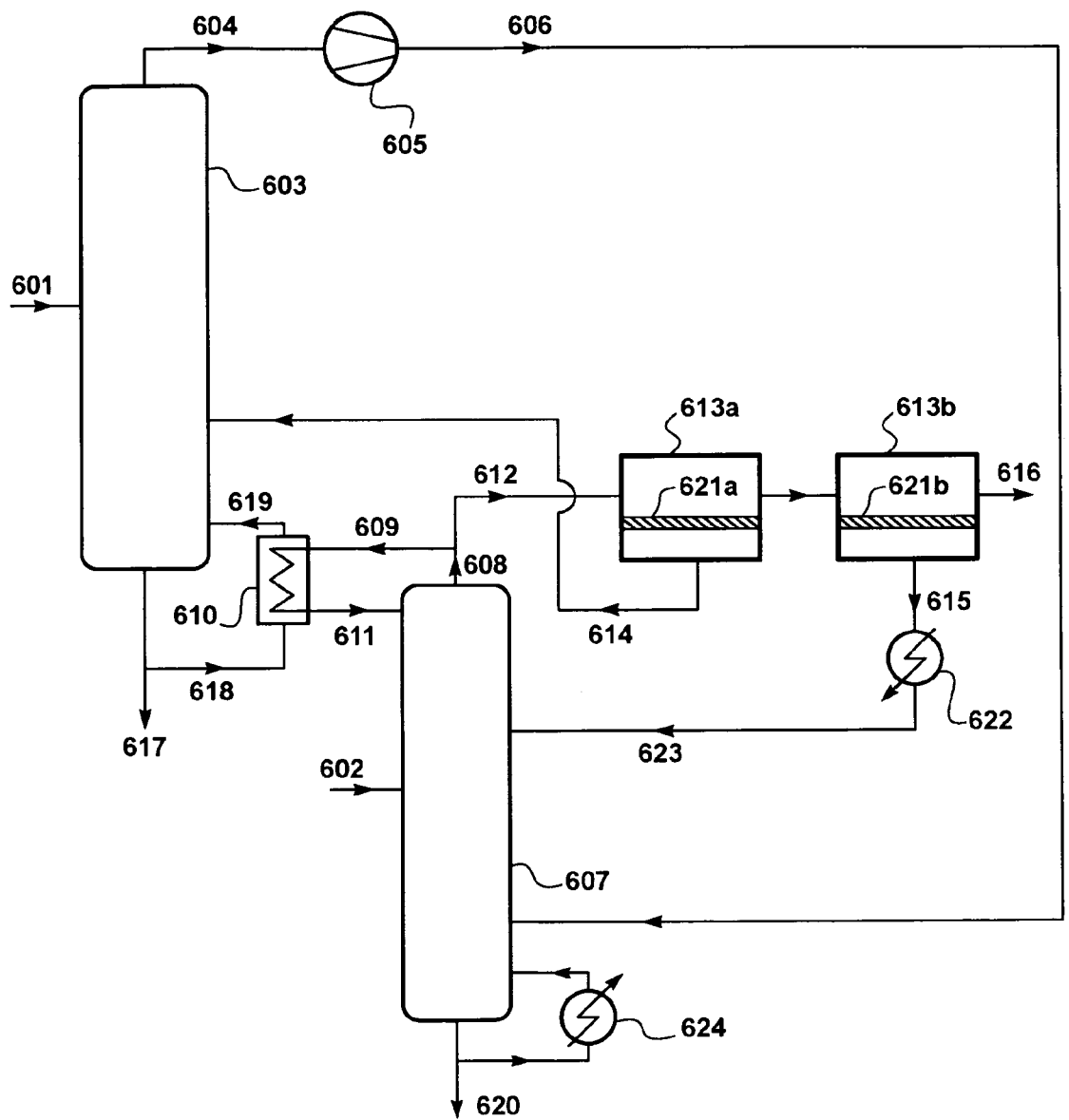
FIG. 6 is a schematic drawing showing a specific embodiment of the process arrangement of FIG. 5, with two membrane separation steps.

A computer calculation was performed with ChemCad 5.5.1 (ChemStations, Inc., Houston, Tex.) to illustrate the process of the invention in the embodiment shown in FIG. 6.

This embodiment is a specific case of the embodiment of FIG. 5, in that the raw feed is split between the two columns, and is similar to the embodiment of FIG. 4 in that two membrane separation steps are used, and the comments and preferences describing those figures should be referred to above.

In this embodiment, raw feeds, 601 and 602, are introduced into columns 603 and 607 respectively. Column 601 is equipped with a reboiler heat exchanger, 610, in which a portion, 618, of the liquid bottoms stream, 617, is evaporated for return to the column as stream, 619.

Overhead stream, 604, is compressed, 605, and passed as compressed vapor stream, 606, to second column 607, which, in this example, is assumed to be equipped with a small reboil loop, 624. Bottoms stream, 620, is withdrawn from the column.

Reflux liquid for this column is provided by heat exchanger 610, in which a portion, 609, of overhead stream, 608, is condensed, then returned to the column as liquid stream, 611.

Overhead vapor that is not sent for reflux is passed as stream, 612, to membrane separation steps, 613a and b, containing membranes 621a and b. First permeate stream, 614 is returned as vapor to the first column; second permeate stream, 615, is condensed, 622, and returned as stream, 623, to the second column.

The second membrane unit produces dehydrated product residue stream, 616, which was assumed to be condensed by heat exchange against incoming feeds 601 and 602.

The calculation assumed that the feed composition was 11.5% ethanol and 88.5% water, representative of a raw feed from a bioethanol manufacturing process. The first column was assumed to have 15 stripping stages, and the second column was assumed to have 15 rectification stages. The columns were assumed to operate at 0.5 bar and 3 bar respectively. The feed was assumed to be distributed between the first and second columns in the ratio 80:20.

The process was configured to provide a rectified overhead stream, 612, containing about 85 wt % ethanol, and a dehydrated product stream, 616, containing 99.7 wt % ethanol.

The membranes in both membrane separation steps were assumed to have a selectivity for water over ethanol of about 30 and a water permeance of 2,000 gpu.

The results of the calculations are summarized in Table 8.

TABLE 8

| | Stream | | | | | | | | |
|---|---|---|---|---|---|---|---|---|---|
| | 601 (1st Feed) | 602 (2nd Feed) | 606 | 612 (Rectified overhead) | 614 | 615 | 616 (Product ethanol) | 617 | 620 |
| Flow (kg/h) | 117,150 | 47,850 | 22,832 | 27,951 | 2,513 | 6,550 | 18,888 | 96,830 | 49,281 |
| Temp (° C.) | 37 | 124 | 191 | 110 | 112 | 110 | 91 | 81 | 134 |
| Pressure (bar) | 1.0 | 3.0 | 3.0 | 3.0 | 0.5 | 0.1 | 3.0 | 0.5 | 3.0 |
| | | | | Component | | | | | |
| Water | 88.5 | 88.5 | 37.7 | 15.0 | 66.3 | 37.7 | 0.3 | 99.9 | 99.9 |
| Ethanol | 11.5 | 11.5 | 62.3 | 85.0 | 33.7 | 62.3 | 99.7 | 0.1 | 0.1 |

The total energy usage for the process was calculated to be only 39.0 million Btu/h, and the energy to operate the compressor was calculated to be only 12.8 million Btu/h, making this a particularly preferred embodiment. The total membrane area used was 4,840 m$^2$.

Example 9

A computer calculation was performed using the same basic assumptions as for Example 8. In this case, however, it was assumed that the feed to the first column contained 11.5 wt % ethanol, consistent with ethanol production from corn, and the feed to the second column contained only 5 wt % ethanol, consistent with ethanol production from corn stover.

The results of the calculations are summarized in Table 9.

TABLE 9

| | Stream | | | | | | | | |
|---|---|---|---|---|---|---|---|---|---|
| | 601 (1st Feed) | 602 (2nd Feed) | 606 | 612 (Rectified overhead) | 614 | 615 | 616 (Product ethanol) | 617 | 620 |
| Flow (kg/h) | 136,400 | 65,210 | 26,296 | 27,852 | 2,503 | 6,527 | 18,821 | 112,607 | 70,179 |
| Temp (° C.) | 37 | 124 | 191 | 110 | 112 | 110 | 91 | 81 | 134 |
| Pressure (bar) | 1.0 | 3.0 | 3.0 | 3.0 | 0.5 | 0.1 | 3.0 | 0.5 | 3.0 |
| | | | | Component | | | | | |
| Water | 88.5 | 95.0 | 37.6 | 15.0 | 66.3 | 37.7 | 0.3 | 99.9 | 99.9 |
| Ethanol | 11.5 | 5.0 | 62.4 | 85.0 | 33.7 | 62.3 | 99.7 | 0.1 | 0.1 |

The total energy usage for the process was calculated to be 44.7 million Btu/h, and the energy to operate the compressor was calculated to be 14.8 million Btu/h.

Example 10

A computer calculation was performed using the same basic assumptions as for Example 8. In this case, however, it was assumed that the feed contained only 3 wt %, and that the feed was distributed between the first and second columns in the ratio 65:35.

The results of the calculations are summarized in Table 10.

TABLE 10

| | Stream | | | | | | | |
|---|---|---|---|---|---|---|---|---|
| | 601 (1st Feed) | 602 (2nd Feed) | 606 | 612 (Rectified overhead) | 614 | 615 | 616 (Product ethanol) | 617 | 620 |
| Flow (kg/h) | 418,283 | 230,217 | 30,562 | 27,941 | 2,511 | 6,548 | 18,881 | 390,321 | 239,382 |
| Temp (° C.) | 37 | 124 | 218 | 110 | 112 | 110 | 91 | 81 | 134 |
| Pressure (bar) | 1.0 | 3.0 | 3.0 | 3.0 | 0.5 | 0.1 | 3.0 | 0.5 | 3.0 |
| | Component | | | | | | | |
| Water | 97.0 | 97.0 | 57.4 | 15.0 | 66.3 | 37.7 | 0.3 | 99.9 | 99.9 |
| Ethanol | 3.0 | 3.0 | 42.6 | 85.0 | 33.7 | 62.3 | 99.7 | 0.1 | 0.1 |

The total energy usage for the process was calculated to be 106 million Btu/h, and the energy to operate the compressor was calculated to be 21.3 million Btu/h.

Example 11

A computer calculation was performed using the same basic assumptions as for Example 8. In this case, however, it was assumed that the embodiment was similar to that shown in FIG. 5, using only one membrane separation step. The permeate stream, 514, was assumed to be condensed, thereby lowering the permeate side pressure to 0.1 bar, with the condensate returned to the second column. The feed was assumed to be distributed between the first and second columns in the ratio 80:20.

The results of the calculations are summarized in Table 11.

TABLE 11

| | Stream | | | | | | | |
|---|---|---|---|---|---|---|---|---|
| | 501 (1st Feed) | 502 (2nd Feed) | 506 | 512 (Rectified overhead) | 514 | 616 (Product ethanol) | 517 | 520 |
| Flow (kg/h) | 117,150 | 47,850 | 21,464 | 27,469 | 8,884 | 18,885 | 95,685 | 41,846 |
| Temp (° C.) | 37 | 124 | 190 | 113 | 30 | 91 | 81 | 134 |
| Pressure (bar) | 1.0 | 3.0 | 3.0 | 3.0 | 0.1 | 3.0 | 0.5 | 3.0 |
| | Component | | | | | | | |
| Water | 88.5 | 88.5 | 37.7 | 15.0 | 47.3 | 0.3 | 99.9 | 99.9 |
| Ethanol | 11.5 | 11.5 | 62.3 | 85.0 | 52.7 | 99.7 | 0.1 | 0.1 |

The total energy usage for the process was calculated to be 43 million Btu/h, and the energy to operate the compressor was calculated to be 12.0 million Btu/h. The total membrane area used was 4,330 m$^2$.

This example differs from Example 8 only in the use of one rather than two membrane separation steps. As can be seen, the process uses slightly more energy but requires a lower membrane area.

Example 12

A computer calculation was performed using the same basic assumptions as for Example 1. In this case, however, it was assumed that the embodiment was similar to that shown in FIG. 8, with a compression step after each column, and using a vacuum pump to lower the pressure on the second permeate side to 20 torr.

The first column was assumed to operate at 0.5 bar and to provide 12 stripping stages; the second was assumed to operate at 1.6 bar and to provide 12 stages of dephlegmation.

The first permeate was assumed to be returned as vapor to the second column; the second permeate was assumed to be condensed against the reboil stream for the first column.

As with the previous embodiments, the process was assumed to treat 165,000 kg/h of feed containing 11.5 wt % ethanol, and to yield a product containing 0.3 wt % water. The product was assumed to be condensed against the reboil stream for the first column.

The bottoms stream from the second column was assumed to be cooled by heat exchange against the reboil stream for the first column, then recirculated as part of the feed to the first column.

The energy needed to heat the reboil stream for the first column was thus assumed to be supplied by the cooling duty of the dephlegmator, the condenser duties for the product and the second permeate, and the cooling of the dephlegmator bottoms stream. The calculated energy balance for the process is shown in Table 12.

TABLE 12

| Component | Heat (+) or cooling (−) duty |
|---|---|
| Reboil energy for stripper column | +157 MMBtu/h |
| Dephlegmator cooling duty | −112 MMBtu/h |
| Product condenser duty | −39 MMBtu/h |
| Permeate condenser duty | −6.9 MMBtu/h |
| Dephlegmator bottoms cooling | −3.3 MMBtu/h |
| Net heat duty for reboiler | Less than zero (−4.2) |
| Compression energy, first overhead compressor | 1,979 kW-h |
| Compression energy, second overhead compressor | 385 kW-h |
| Compression energy, vacuum pump | 544 kW-h |
| Total pump energy | 2908 kW-h = 29.1 MMBtu/h |

As can be seen, all of the energy need to provide a reboil stream for the first column can be provided by heat recovered from other steps in the process, so that no external heating for this stream need be provided. The total energy to operate the process is thus the energy required to operate the three pumps, which, based on the same conversion from kW-h to MMBtu as used above, gives a total energy consumption for the process of 29.1 MMBtu.

The required membrane area was calculated to be 721 m$^2$ for the first membrane separation step and 1,405 m$^2$ for the second step, or 2,126 m$^2$ total.

Compared with the processes modeled in the previous examples, the energy consumption and membrane area for this process is very modest.

We claim:

1. A process for recovering an organic solvent from a solvent and water mixture, comprising:
   (a) subjecting at least a portion of the mixture to a first distillation step, carried out by passing a first feed stream of the mixture, at a first pressure, into a first column having a reboiler system, to produce a solvent-enriched, first overhead vapor stream and a bottoms stream, wherein the bottoms stream consists essentially of water;
   (b) compressing at least a portion of the first overhead vapor stream to form a compressed overhead vapor stream;
   (c) subjecting the compressed overhead vapor stream to a second distillation step, carried out at a second pressure that is higher than the first pressure, in a second column having a reflux condenser system, to produce a solvent-enriched, second overhead vapor stream;
   (d) performing a first membrane separation step, comprising:
      (i) providing a first membrane having a first feed side and a first permeate side, the membrane being selective in favor of water over solvent;
      (ii) passing at least a portion of the second overhead vapor stream at a first feed pressure across the first feed side;
      (iii) maintaining a first permeate pressure on the first permeate side that is lower than the first feed pressure;
      (iv) withdrawing from the first feed side, as a first residue stream, a dehydrated solvent product;
      (v) withdrawing from the first permeate side a first permeate stream enriched in water compared with the second overhead vapor stream;
   (e) recovering heat by:
      (i) providing a heat exchanger that forms at least part of the reflux condenser system and at least part of the reboiler system;
      (ii) passing a reflux stream withdrawn from the second column through the heat exchanger;
      (iii) passing a reboil stream withdrawn from the first column through the heat exchanger in heat exchanging relationship with the reflux stream; and
   (f) recirculating the first permeate stream within the process to a distillation step selected from the group consisting of the first distillation step and the second distillation step.

2. The process of claim 1, wherein the first permeate stream is condensed and recirculated as liquid to the second distillation step.

3. The process of claim 1, wherein latent heat of condensation is recovered from the first residue stream by bringing the first residue stream into heat exchanging contact with the first feed stream.

4. The process of claim 1, wherein latent heat of condensation is recovered from the first residue stream by bringing the first residue stream into heat exchanging contact with the reboil stream.

5. The process of claim 1, wherein the first membrane has a selectivity in favor of water over solvent of less than 100.

6. The process of claim 1, wherein the first distillation step comprises a first stripping step and a first rectification step.

7. The process of claim 1, wherein the second distillation step comprises a second stripping step and a second rectification step.

8. The process of claim 1, further comprising compressing at least a portion of the second overhead vapor stream before passing the stream to step (d).

9. The process of claim 1, further comprising passing a second portion of the mixture as a second feed stream into the second column.

10. The process of claim 1, further comprising recovering additional solvent from a second solvent and water mixture by passing at least a portion of the second solvent and water mixture as a second feed stream into the second column.

11. The process of claim 1, wherein the first permeate stream is recirculated as vapor to the first distillation step.

12. The process of claim 1, wherein the second distillation step is operated in such a manner as to provide a solvent concentration in the range 75-85 wt % in the second overhead vapor stream.

13. The process of claim 1, wherein the mixture has a solvent concentration below 5 wt %.

14. The process of claim 1, wherein the solvent is chosen from the group consisting of alcohols, aldehydes, ketones, esters and organic acids having no more than six carbon atoms.

15. The process of claim 1, wherein the solvent comprises ethanol.

16. The process of claim 1, further comprising:
   (g) performing a second membrane separation step, comprising:
      (i) providing a second membrane having a second feed side and a second permeate side, the membrane being selective in favor of water over solvent;
      (ii) passing at least a portion of the first residue stream at a second feed pressure across the second feed side;
      (iii) maintaining a second permeate pressure on the second permeate side that is lower than the second feed pressure;
      (iv) withdrawing from the second feed side, as a second residue stream, a further dehydrated solvent product;
      (v) withdrawing from the second permeate side a second permeate stream enriched in water compared with the first residue stream.

17. The process of claim 16, wherein the second permeate pressure is lower than the first permeate pressure.

18. The process of claim 16, further comprising lowering the second permeate pressure by cooling and condensing the second permeate stream.

19. The process of claim 16, further comprising condensing the second permeate stream and returning it as liquid to the second distillation step.

20. The process of claim 16, wherein the first permeate stream is recirculated as vapor to the first distillation step.

21. The process of claim 16, wherein latent heat of condensation is recovered from the second residue stream by bringing the second residue stream into heat exchanging contact with the reboil stream.

22. The process of claim 16, wherein latent heat of condensation is recovered from the second residue stream by bringing the second residue stream into heat exchanging contact with the first feed stream.

23. A process for recovering an organic solvent from a solvent and water mixture, comprising:
   (a) subjecting at least a portion of the mixture to a first distillation step, carried out by passing a first feed stream of the mixture, at a first pressure, into a first column having a reboiler system, to produce a solvent-enriched, first overhead vapor stream and a bottoms stream, wherein the bottoms stream consists essentially of water;

(b) compressing at least a portion of the first overhead vapor stream to form a compressed overhead vapor stream;

(c) subjecting the compressed overhead vapor stream to a second distillation step, carried out at a second pressure that is higher than the first pressure, in a second column having a reflux condenser system, to produce a solvent-enriched, second overhead vapor stream;

(d) performing a first membrane separation step, comprising:
  (i) providing a first membrane having a first feed side and a first permeate side, the membrane being selective in favor of water over solvent;
  (ii) passing at least a portion of the second overhead vapor stream at a first feed pressure across the first feed side;
  (iii) maintaining a first permeate pressure on the first permeate side that is lower than the first feed pressure;
  (iv) withdrawing from the first feed side a partially dehydrated first residue stream;
  (v) withdrawing from the first permeate side a first permeate stream enriched in water compared with the second overhead vapor stream;

(e) performing a second membrane separation step, comprising:
  (i) providing a second membrane having a second feed side and a second permeate side, the membrane being selective in favor of water over solvent;
  (ii) passing at least a portion of the first residue stream at a second feed pressure across the second feed side;
  (iii) maintaining a second permeate pressure on the second permeate side that is lower than the second feed pressure;
  (iv) withdrawing from the second feed side, as a second residue stream, a further dehydrated solvent product;
  (v) withdrawing from the second permeate side a second permeate stream enriched in water compared with the first residue stream;

(f) performing a step selected from the group consisting of steps (g) and (h) as follows:

(g) recovering heat by:
  (i) providing a heat exchanger that forms at least part of the reflux condenser system and at least part of the reboiler system;
  (ii) passing a reflux stream withdrawn from the second column through the heat exchanger;
  (iii) passing a reboil stream withdrawn from the first column through the heat exchanger in heat exchanging relationship with the reflux stream;

(h) recirculating at least one of the permeate streams within the process to a distillation step selected from the group consisting of the first distillation step and the second distillation step.

24. The process of claim 23, wherein both step (g) and step (h) are performed.

25. A process for producing a light alcohol, comprising the following steps:

(a) fermenting a sugar to form a fermentation broth comprising the alcohol and water;

(b) subjecting at least a portion of the fermentation broth to a first distillation step, carried out by passing a first feed stream of the fermentation broth, at a first pressure, into a first column having a reboiler system, to produce an alcohol-enriched, first overhead vapor stream and a bottoms stream, wherein the bottoms stream consists essentially of water;

(c) compressing at least a portion of the first overhead vapor stream to form a compressed overhead vapor stream;

(d) subjecting the compressed overhead vapor stream to a second distillation step, carried out at a second pressure that is higher than the first pressure, in a second column having a reflux condenser system, to produce an alcohol-enriched, second overhead vapor stream;

(e) performing a first membrane separation step, comprising:
  (i) providing a first membrane having a first feed side and a first permeate side, the membrane being selective in favor of water over alcohol;
  (ii) passing at least a portion of the second overhead vapor stream at a first feed pressure across the first feed side;
  (iii) maintaining a first permeate pressure on the first permeate side that is lower than the first feed pressure;
  (iv) withdrawing from the first feed side, as a first residue stream, a dehydrated alcohol product;
  (v) withdrawing from the first permeate side a first permeate stream enriched in water compared with the second overhead vapor stream;

(f) recovering heat by:
  (i) providing a heat exchanger that forms at least part of the reflux condenser system and at least part of the reboiler system;
  (ii) passing a reflux stream withdrawn from the second column through the heat exchanger;
  (iii) passing a reboil stream withdrawn from the first column through the heat exchanger in heat exchanging relationship with the reflux stream; and (g) recirculating the first permeate stream within the process to a destination selected from the group consisting of the fermentation step (a), the first distillation step (b) and the second distillation step (d).

26. The process of claim 25, wherein the sugar has been prepared by conversion of a plant biomass that comprises a starch or a cellulose.

27. The process of claim 25, wherein the alcohol comprises ethanol.

28. The process of claim 25, further comprising performing a filtration step between steps (a) and (b).

29. The process of claim 25, wherein latent heat of condensation is recovered from the first residue stream by bringing the first residue stream into heat exchanging contact with the first feed stream.

30. The process of claim 25, wherein latent heat of condensation is recovered from the first residue stream by bringing the first residue stream into heat exchanging contact with the reboil stream.

31. The process of claim 25, wherein the first membrane has a selectivity in favor of water over alcohol of less than 100.

32. The process of claim 25, wherein the first distillation step comprises a first stripping step and a first rectification step.

33. The process of claim 25, wherein the second distillation step comprises a second stripping step and a second rectification step.

34. The process of claim 25, further comprising passing a second portion of the mixture as a second feed stream into the second column.

35. The process of claim 25, further comprising recovering additional alcohol from a second alcohol and water mixture by passing at least a portion of the second alcohol and water mixture as a second feed stream into the second column.

36. The process of claim 25, further comprising:
(h) performing a second membrane separation step, comprising:

(i) providing a second membrane having a second feed side and a second permeate side, the membrane being selective in favor of water over alcohol;
(ii) passing at least a portion of the first residue stream at a second feed pressure across the second feed side;
(iii) maintaining a second permeate pressure on the second permeate side that is lower than the second feed pressure;
(iv) withdrawing from the second feed side, as a second residue stream, a further dehydrated ethanol product;
(v) withdrawing from the second permeate side a second permeate stream enriched in water compared with the first residue stream.

37. The process of claim 36, wherein the second permeate pressure is lower than the first permeate pressure.

38. The process of claim 36, further comprising lowering the second permeate pressure by cooling and condensing the second permeate stream.

39. The process of claim 36, further comprising condensing the second permeate stream and returning it as liquid to the second distillation step.

40. The process of claim 36, wherein latent heat of condensation is recovered from the second residue stream by bringing the second residue stream into heat exchanging contact with the reboil stream.

41. The process of claim 36, wherein latent heat of condensation is recovered from the second residue stream by bringing the second residue stream into heat exchanging contact with the first feed stream.

42. The process of claim 36, further comprising passing a second portion of the fermentation broth as a second feed stream into the second column.

43. The process of claim 36, further comprising recovering additional alcohol from a second alcohol and water mixture by passing at least a portion of the second alcohol and water mixture as a second feed stream into the second column.

* * * * *

UNITED STATES PATENT AND TRADEMARK OFFICE
CERTIFICATE OF CORRECTION

| | |
|---|---|
| PATENT NO. | : 8,114,255 B2 |
| APPLICATION NO. | : 12/229802 |
| DATED | : February 14, 2012 |
| INVENTOR(S) | : Leland M Vane et al. |

It is certified that error appears in the above-identified patent and that said Letters Patent is hereby corrected as shown below:

On the title page, item (73), the assignee data should correctly read:

United States Environmental Protection Agency, Washington, District of Columbia, and Membrane Technology and Research, Inc, Menlo Park, CA Signed and Sealed this
Twenty-third Day of July, 2013

Teresa Stanek Rea
*Acting Director of the United States Patent and Trademark Office*